US00PP13061P2

(12) United States Plant Patent
Chandler

(10) Patent No.: US PP13,061 P2
(45) Date of Patent: Oct. 8, 2002

(54) 'EARLIBRITE' STRAWBERRY PLANT

(76) Inventor: Craig K. Chandler, Gulf Coast REC—Dover—13138 Lewis Gallagher Rd., Dover, FL (US) 33527-9664

( * ) Notice: Subject to any disclaimer, the term of this patent is extended or adjusted under 35 U.S.C. 154(b) by 0 days.

(21) Appl. No.: 09/570,128

(22) Filed: May 12, 2000

(51) Int. Cl.[7] ..... A01H 5/00
(52) U.S. Cl. ..... Plt./208
(58) Field of Search ..... Plt./208

*Primary Examiner*—Bruce R. Campell
*Assistant Examiner*—Michelle Kizilkaya

(57) ABSTRACT

A new and distinct variety of strawberry (*Fragaria*× *ananassa*), which originated from seed produced by a hand-pollinated cross between 'Rosa Linda' and FL 90-38. The new strawberry, named 'Earlibrite', is distinguished by its compact plant habit and its high November through February production of large, bright red fruit when grown in Dover, Fla. or other areas that have a subtropical climate similar to that of Dover.

1 Drawing Sheet

BACKGROUND OF THE NEW VARIETY

The present invention relates to a new and distinct variety of strawberry (*Fragaria*×*ananassa*Duchesne) plant which is named 'Earlibrite' and more particularly to a strawberry plant that is distinguished by its compact plant habit and its high early season (December through February) production of large, bright red fruit when grown in a mild (subtropical) winter climate. Asexual propagation was performed at Dover, Fla. where the selection was made and plants were tested. Contrast is made to 'Sweet Charlie' (U.S. Plant Pat. No. 8,729) and 'Camarosa' (U.S. Plant Pat. No. 8,708), standard varieties, for reliable description. This new variety is a promising candidate for commercial success in that it has high early season fruit production like 'Sweet Charlie', but tends to have larger and firmer fruit than 'Sweet Charlie'.

ORIGIN OF THE VARIETY

This strawberry plant (genotype) originated in a strawberry breeding plot at Dover, Fla. The seed parent was 'Rosa Linda' (U.S. Plant Pat. No. 9,866), a strawberry variety with a desirable fruit shape and high early season yield potential. The pollen parent was FL 90-38, a non-patented University of Florida breeding selection with an ability to produce attractive fruit early in the season. The seeds resulting from the controlled hybridization were germinated in a greenhouse and the resulting seedlings were planted and allowed to produce daughter plants by asexual propagation (i.e. by runners). Two daughter plants from each seedling were transplanted to raised beds, where they fruited. 'Earlibrite' strawberry (as represented by two daughter plants from the original seedling) exhibited large attractive fruit, and therefore was selected for further evaluation. 'Earlibrite' was selected from among 207 sibling genotypes as the $100^{th}$ selection of the 1993–94 season, and thus was designated FL 93-100. It has been asexually propagated by runners, annually, and further test plantings have established that the vegetative and fruit characteristics of the propagules are identical to the initial two daughter plants.

SUMMARY THE VARIETY

'Earlbrite', when grown in a subtropical fall and winter climate, is set apart from all other strawberry plants by a combination of three characteristics: compact plant habit, large fruit (averaging>20 gram per berry), and high November through February production (approximately 20,000 pounds of marketable fruit per acre in commercial trials).

BRIEF DESCRIPTION OF THE DRAWING

The accompanying photographs show a typical specimen of the plant and fruit of the new variety in color.

DETAILED BOTANICAL DESCRIPTION

The following botanical description is that of the variety grown under the ecological conditions prevailing at Dover, Fla. Colors are described using the Pantone® Color Formula Guide.

'Earlibrite' is a short day cultivar. It has a more compact plant habit than 'Sweet Charlie' or 'Camarosa', currently the standard strawberry cultivars grown in west-central Florida. Average height and width for mature plants is 18cm and 28 cm respectively. Average petiole length and diameter is 108 mm and 4 mm respectively, and petioles have a medium pubescence. Average length and breadth of terminal leaflets is 81 and 71 mm respectively. Average length and breadth of secondary leaflets is 75 and 72 mm respectively. Leaflet margins are crenate and average 23 serrations per leaflet. The upper leaf surface is a dark grey green (Pantone® 575); the lower leaf surface is a light grey green (Pantone® 5767); and the petiole is a medium yellow green (Pantone® 583). The compact plant habit leads to the production of fruit that are exposed, and therefore easy to harvest. This exposure, however, also makes the fruit vulnerable to rain damage (i.e. cracking and cat-facing). Flowers open at or below canopy height, and have an average of 6.5 petals and 28 stamens. Individual petals have a length of 1.0 cm and a width of 1.1 cm. The diameter of the corolla (i.e. the petals collectively) is 2.7 cm. The color of the calyx is yellow green (Pantone® 364). Pedicels attached to mature primary fruit are 125 to 167 mm long, 3 mm in diameter, and yellow green (Pantone® 384), with branching of the inflorescence usually occurring very close to the crown. Fruit of 'Earlibrite' tend to be very large. Marketable fruit of 'Earlibrite' had an average weight of over 20 g in trials at Dover, Fla. (Table 1). Primary fruit are often globose-conic in shape (often weighing 30–40 g); whereas secondary and tertiary fruit are conic to wedge-shaped (weighing 15–30 g). External fruit color is a deep orange red (Pantone® 1805); internal color is a warm red (Pantone® Warm Red). The achenes are generally protruding, with about half the achene above the fruit surface. Achenes are a yellow green (Pantone® 3975). The calyx is generally medium in size and slightly recurved. Fruit of 'Earlibrite' are moderately firm, but very juicy, and have a flavor intensity and sweetness comparable to 'Sweet Charlie' and 'Camarosa', as determined by a trained taste panel (Table 2). 'Earlibrite' also has some of the aromatic qualities of its parent 'Rosa Linda'. The preferred planting time for 'Earlibrite' is September 25 to October 10 in central Florida. 'Earlibrite', in replicated plot trials at Dover, Fla. produced total yields not significantly different than those of the standard cultivars (Table 1). 'Earlibrite' in the 1996–97 trial produced a significantly higher December fruit yield than 'Sweet Charlie' and 'Camarosa'. The 1996–97 trial was the only trial reported in Table 1 where the plants of 'Earlibrite', 'Sweet Charlie', and 'Camarosa' all came from the same nursery area. Nursery location is known to influence early fruit yield in the Florida winter production system. 'Earlilbrite' is self-fruitful, and can be grown in large solid blocks. 'Earlibrite' grown in three commercial fields in the Dover/Plant City, Fla. area during the 1999–2000 season produced early-season fruit yields comparable to those of 'Sweet Charlie'. 'Earlibrite' has also been an early producer of large fruit in observational plots in north Florida, but in this location it generally lacks vigor and is less productive than 'Camarosa' or 'Chandler' (U.S. Plant Pat. No. 5,262). 'Earlibrite' is susceptible to anthracnose fruit rot (caused by *Colletotrichum acutatum* Simmonds), but, in most years, this disease should not be a serious problem because growers will probably finish harvesting 'Earlibrite' in late February or early March, which is typically before environmental conditions are favorable for disease development. 'Earlibrite' is less susceptible than 'Sweet Charlie' to Botrytis fruit rot (caused by *Botrytis cinerea* Pers.ex Fr.) and less susceptible than 'Camarosa' to powdery mildew (caused by *Sphaerotheca macularis* [Wallr.:Fr.] Jacz. F. sp. Fragariae Peries). 'Earlibrite' can, however, be severely affected by the twospotted spider mite (*Tetranychus urticae* Koch). DNA banding patterns for 'Earlibrite', 'Sweet Charlie', 'Camarosa', 'Rosa Linda', and 'Oso Grande' (U.S. Plant Pat. No. 6,578) are presented in Table 3.

TABLE 1

Performance of 'Earlibrite' strawberry compared with two standard cultivars grown at Dover, Florida[z]

| Cultivar | Marketable yield[y] (g/plant) December | January | February | March | Total | Weight/ fruit[x] (g) |
|---|---|---|---|---|---|---|
| | | | 1995–96 | | | |
| Earlibrite | 0 b[w] | 109 a | 256 a | 122 a | 488 a | 27.0 a |
| Sweet Charlie | 18 a | 84 a | 174 ab | 178 a | 454 a | 17.1 c |
| Oso Grande | 0 b | 84 a | 87 b | 174 a | 344 a | 23.1 b |
| | | | 1996–97 | | | |
| Earlibrite | 115 a | 120 a | 266 a | 71 b | 572 a | 21.7 a |
| Sweet Charlie | 73 b | 98 a | 250 a | 62 b | 483 a | 17.8 c |
| Camarosa | 77 b | 131 a | 212 a | 137 a | 557 a | 20.2 b |

TABLE 1-continued

Performance of 'Earlibrite' strawberry compared with two standard cultivars grown at Dover, Florida[z]

| Cultivar | Marketable yield[y] (g/plant) December | January | February | March | Total | Weight/ fruit[x] (g) |
|---|---|---|---|---|---|---|
| | | | 1997–98 | | | |
| Earlibrite | 66 b | 110 a | 189 ab | 280 b | 645 a | 20.7 a |
| Sweet Charlie | 91 a | 54 b | 219 a | 257 b | 622 a | 17.6 b |
| Camarosa | 50 b | 105 a | 167 b | 426 a | 748 a | 20.0 a |

[z]Transplants were obtained from the following nursery locations: 'Earlibrite' from Florida in 1995 and 1997, and Canada in 1996; 'Sweet Charlie' from Canada in 1995 and 1996, and Florida in 1997; 'Oso Grande' from Canada; and 'Camarosa' from Canada in 1996, and North Carolina in 1997.

Planting dates were Nov. 9, 1995, Oct. 15, 1996, and Oct. 9, 1997.

[y]Values represent mean per plant yield for three 10-plant plots in 1995–96, four 16-plant plots in 1996–97, and four 10-plant plots in 1997–98.

[x]Mean fruit weight was determined by dividing total marketable fruit yield per plot by total marketable fruit number per plot.

[w]Mean separation within columns and seasons by Fisher's protected least significant difference test, $P \leqq 0.05$.

TABLE 2

Sensory characteristics of 'Earlibrite' strawberry fruit compared to two standard cultivars grown at Dover, Florida[z]

| Cultivar | Color uniformity[y] | Flavor intensity[y] | Sweetness[y] | Firmness[y] |
|---|---|---|---|---|
| | | 1996–97 | | |
| Earlibrite | 9.5 (1.9) | 7.4 (1.25) | 6.7 (1.05) | 7.7 (0.10) |
| Sweet Charlie | 9.5 (1.5) | 6.9 (0.70) | 6.4 (1.0) | 6.4 (0.35) |
| Camarosa | 11.1 (0.25) | 8.5 (0.05) | 7.4 (0.15) | 10.2 (0.8) |
| | | 1997–98 | | |
| Earlibrite | 8.9 (0.33) | 8.2 (0.64) | 7.3 (0.69) | 10.2 (0.32) |
| Sweet Charlie | 9.9 (0.42) | 7.8 (0.54) | 7.2 (0.53) | 8.2 (0.57) |
| Camarosa | 9.7 (0.79) | 7.5 (0.35) | 6.0 (0.26) | 11.7 (0.62) |

[z]Means based on the ratings of 12 to 15 trained panelists who rated samples of fruit from each cultivar twice in 1997 and three times in 1998. Standard Errors in parentheses.

[y]Rating scale 1 to 15, with a higher score indicating more uniform color, more strawberry flavor intensity, more sweetness, and more firmness.

TABLE 3

DNA marker analysis[z]

| Variety | Primer B06 | B07 | B14 | X11 | X06 |
|---|---|---|---|---|---|
| | Band number for each primer and DNA pattern | | | | |
| Earlibrite | 1234 | 12 | 12345 | 12 | 12 |
| Rosa Linda | 0000 | 11 | 00000 | 00 | 11 |
| Sweet Charlie | 0001 | 11 | 00000 | 00 | 11 |
| Camarosa | 0101 | 01 | 00111 | 10 | 01 |
| Oso Grande | 1101 | 10 | 10010 | 10 | 11 |
| | 1001 | 11 | 01010 | 11 | 10 |

TABLE 3-continued

| | DNA marker analysis[z] | | | | |
|---|---|---|---|---|---|
| | Primer | | | | |
| | B06 | B07 | B14 | X11 | X06 |
| | Band number for each primer and DNA pattern | | | | |
| Variety | 1234 | 12 | 12345 | 12 | 12 |

[z]Random amplified polymorphic DNA (RAPD) patterns were determined using primers B06, B07, B14, X06, and X11 from Operon Technologies, Inc. Stolen tip DNA was isolated using Dneasy Plant ™ extraction kit from Qiagen ®, Inc. Amplification reactions were performed in 20 microliter volumes using a procedure adapted from Williams et al., 1990, Nucleic Acids Research 25:6531–6535.

The reagents and conditions included 50 mM Tris (pH 8.3), 0.25 mg/mL bovine serum albumin, 2.1 mM $MgCl_2$, 0.5% Ficoll 400, 1.0 mM tartrazine, 0.2 mM each of dATP, dCTP, dGTP, dTTP, 1.0 mM primer DNA, 0.065 ng strawberry DNA, 1 unit Taq-DNA polymerase (Promega, Inc.).

The reaction conditions were 4 minutes at 94° C., then 10 seconds at 94° C., 1 minute at 45° C., 3.5 minutes at 68° C., then 9 cycles of 10 seconds at 94° C., 1 minute at 45° C., with an incrementation of 0.5 degrees per cycle, 3.5 minutes at 68° C., then 29 cycles of 10 seconds at 94° C., 1 minute at 40° C. and 3.5 minutes at 68° C. with a 10 second extension per cycle. The reactions were incubated in Model PTC-100 thermocycler (MJR, Inc.)

TABLE 3-continued

| | DNA marker analysis[z] | | | | |
|---|---|---|---|---|---|
| | Primer | | | | |
| | B06 | B07 | B14 | X11 | X06 |
| | Band number for each primer and DNA pattern | | | | |
| Variety | 1234 | 12 | 12345 | 12 | 12 |

The reaction products were analyzed wth gel electrophoresis using 1.0% agarose 3:1 high resolution blend (AMRESCO, Inc.) in a running buffer of 0.045 M Tris-Borate, 0.001 M EDTA. The separated DNA was detected using ethidium bromide and viewed with a ultra violet transilluminator. Reproducible polymorphic banding from the electrophoresis analysis was observed with the DNA primers. The amplification reactions resulted with varying levels of polymorphism, from 2 to 5 polymorphic bands depending on primer used. The polymorphic bands were scored as 0 equals absence and 1 equals presence.

We claim:

1. A new and distinct strawberry plant as illustrated and described, characterized by a compact habit, large fruit, and high November through February production when grown in the Dover/Plant City area of Florida.

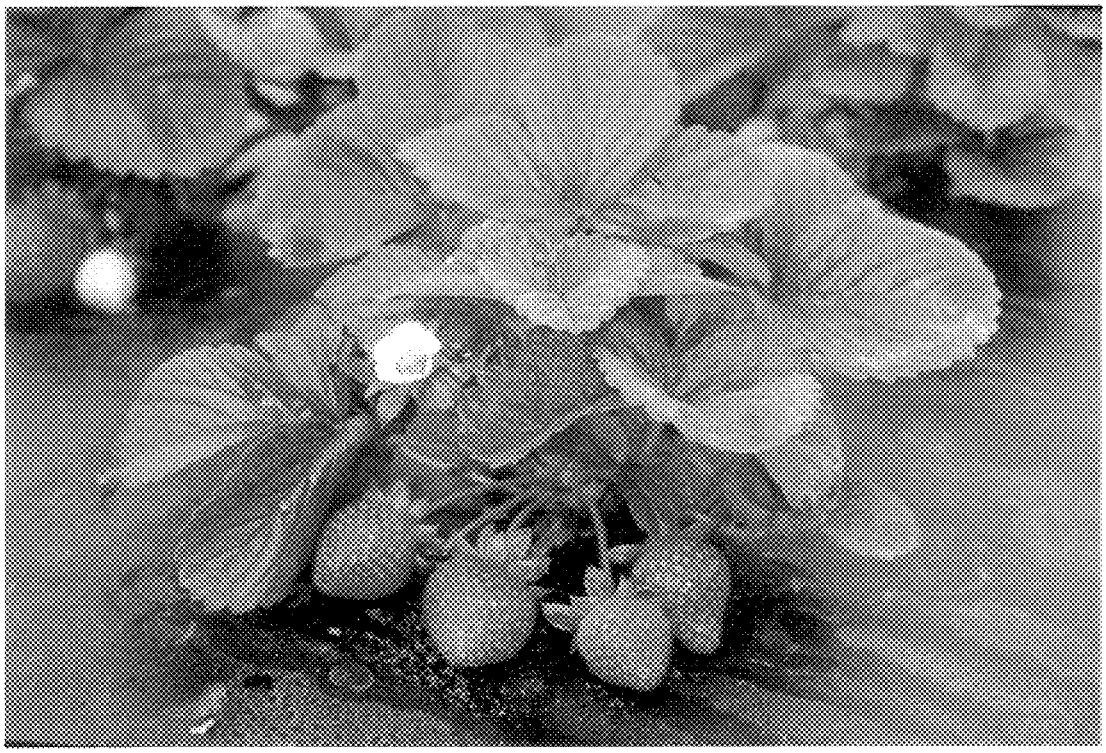

* * * * *